United States Patent [19]

Heinemann et al.

[11] 4,374,846
[45] Feb. 22, 1983

[54] N-AMINO ALKYL INDOLE COMPOUNDS COMPOSITIONS CONTAINING SAME, AND A METHOD OF USING SAME IN THERAPY OF DISORDERS OF GASTROINTESTINAL MOTILITY

[75] Inventors: Henning Heinemann; Heinrich-Wilhelm Ohlendorf, both of Hanover; Klaus-Ulrich Wolf, Haenigsen, all of Fed. Rep. of Germany

[73] Assignee: Kali-Chemie Pharma GmbH, Hanover, Fed. Rep. of Germany

[21] Appl. No.: 172,023

[22] Filed: Jul. 24, 1980

[30] Foreign Application Priority Data

Aug. 2, 1979 [DE] Fed. Rep. of Germany ....... 2931323

[51] Int. Cl.³ .................. C07D 209/38; A61K 31/40; A61K 31/435; C07D 401/06
[52] U.S. Cl. .................................. 424/274; 578/484; 546/201; 424/267
[58] Field of Search .............................. 260/326.13 C; 200/326.14 R; 424/274; 578/787; 546/201

[56] References Cited

U.S. PATENT DOCUMENTS

3,198,807  8/1965  Thiomet .................... 260/326.13 C
3,502,667  3/1970  Makenishi et al. ......... 260/326.13 C

FOREIGN PATENT DOCUMENTS

2727047 12/1977 Fed. Rep. of Germany .
959203   5/1964 United Kingdom .

*Primary Examiner*—Donald G. Daus
*Assistant Examiner*—D. B. Springer
*Attorney, Agent, or Firm*—Schwartz, Jeffery, Schwaab, Mack, Blumenthal & Koch

[57] ABSTRACT

Novel N-amino alkyl indole compounds are disclosed. These compounds correspond to the Formula I

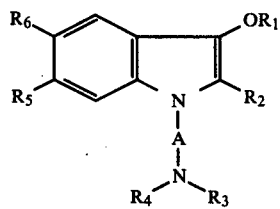

In said Formula
  $R_1$ indicates the hydrogen atom, an alkyl group with 1 to 4 carbon atoms, which may be substituted by a phenyl group, or the acetyl group;
  $R_2$ indicates the hydroxy carbonyl group, an alkoxy carbonyl group with 1 to 4 alkyl carbon atoms, the cyano group, the amino carbonyl group, a mono-alkyl amino carbonyl group with 1 to 4 alkyl carbon atoms, or a di-alkyl amino carbonyl group with 1 to 4 alkyl carbon atoms, with the proviso that, when $R_2$ is the hydroxy carbonyl group, then $R_1$ is other than the hydrogen atom;
  A indicates an alkylene group with 2 to 5 carbon atoms;
  $R_3$ and $R_4$ are the same or different substituents and indicate the hydrogen atom, an alkyl group with 1 to 4 carbon atoms, or $R_3$ and $R_4$ are an alkylene group forming, together with the nitrogen atom to which they are attached, a heterocyclic ring with 5 to 7 ring members; and
  $R_5$ and $R_6$ are the same or different substituents and indicate hydrogen and halogen atoms, alkyl groups with 1 to 3 carbon atoms, alkoxy groups with 1 to 3 carbon atoms, or one of said substituents $R_5$ and $R_6$ being the nitro group or the trifluoro methyl group while the other one is the hydrogen atom.

The acid addition salts of said compounds are also disclosed.

The above mentioned novel N-amino alkyl indole compounds have a favorable effect upon the motility of the gastro-intestinal tract.

The compounds are obtained, for instance, by reacting the alkali metal salts of a corresponding indole compound which is unsubstituted at its nitrogen atom, with a halogeno alkyl amine.

15 Claims, No Drawings

N-AMINO ALKYL INDOLE COMPOUNDS COMPOSITIONS CONTAINING SAME, AND A METHOD OF USING SAME IN THERAPY OF DISORDERS OF GASTROINTESTINAL MOTILITY

BACKGROUND OF THE INVENTION

1. Field of the Invention

The present invention relates to novel and useful N-amino alkyl indole compounds and more particularly to N-amino alkyl indole compounds which are substituted in 2-position by a substituted or unsubstituted hydroxy carbonyl group or by a cyano group, or by an amino carbonyl group and in 3-position by a substituted or unsubstituted hydroxyl group. These compounds may be substituted in 5- and/or 6-position by halogen or an alkyl group or an alkoxy group. One of said substituents in 5- or 6-position may also be a nitro group or a trifluoro methyl group, while the other substituent is hydrogen. Furthermore, this invention relates to pharmaceutically acceptable acid addition salts of said indole compounds as well as to processes of producing said amino alkyl indole compounds and their acid addition salts, to compositions and more particularly to pharmaceutical compositions containing such compounds, and to a method of using such compositions in therapy and more particularly for the treatment of certain gastro-intestinal disorders and diseases.

2. Description of the Prior Art

It is known that a considerable number of gastro-enterological complaints are caused by functional disturbances. Disorders of the motility, more particularly of the stomach and its sphincters, have been recognized more and more as the cause of various diseases and disorders of the gastro-intestinal tract. See, for instance, "Leber, Magen, Darm" (liver, stomach, intestines) vol. 8 (1978) No. 4, pages 177 to 182 and pages 184 to 190 or, respectively, "Internist" vol. 20, 1979, pages 10 to 17. More particularly a pylorus incompetence which is made responsible for the duodeno-gastric reflux, is discussed extensively in connection with a search for the pathologic-physiological causes of various disturbances and disorders of the gastro-intestinal tract. See, for instance, "Digestive Diseases" vol 21, 1976 No. 2, pages 165 to 173. According to these discussions and publications, the reflux gastritis, the ulcus ventriculi and duodeni, as well as the sense of fullness, nausea, and epigastric pain without anatomically recognizable reasons are caused, or are complicated in their course, by disorders of the gastric passage.

Heretofore no satisfactory pharmaceutical agent for treating disorders of the gastro-intestinal motility was known.

SUMMARY OF THE INVENTION

It is one object of the present invention to provide novel and useful N-amino alkyl indole compounds and their acid addition salts.

Another object of the invention is to provide simple and advantageous processes of producing such novel N-amino alkyl indole compounds and their acid addition salts.

Still another object of the present invention is to provide compositions containing such novel N-amino alkyl indole compounds and their acid addition salts, and especially pharmaceutical compositions containing same.

A further object of the present invention is to provide a novel and highly effective method of treating certain gastro-intestinal disorders and diseases by administering such pharmaceutical compositions to patients.

Other objects and advantageous features of the present invention will become apparent as the description proceeds.

In principle the aim of the present invention is to provide the medical profession with novel N-amino alkyl indole compounds having valuable pharmacological and therapeutic properties.

Surprisingly it was found that the novel N-amino alkyl indole compounds have a favorable effect upon gastric motility.

Thus the present invention comprises novel N-amino alkyl indole compounds of the following Formula I

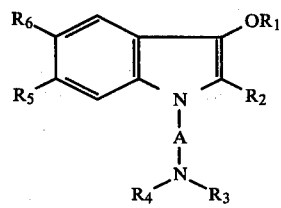

In said formula
  $R_1$ indicates hydrogen, an alkyl group with 1 to 4 carbon atoms which may be substituted by a phenyl group, and especially a benzyl group, or an acyl group and especially an acetyl group;
  $R_2$ indicates a hydroxy carbonyl group, an alkoxy carbonyl group with 1 to 4 carbon atoms in the alkyl group, a cyano group, an amino carbonyl groiup, a mono-alkyl amino carbonyl group, or a di-alkyl amino carbonyl group with 1 to 4 carbon atoms in the alkyl groups, with the proviso that, when $R_2$ is a hydroxy carbonyl group, $R_1$ is another substituent than hydrogen;
  A indicates an alkylene group with 2 to 5 carbon atoms;
  $R_3$ and $R_4$ are the same or different substituents and indicate hydrogen, alkyl groups with 1 to 4 carbon atoms, or alkylene groups which, together with the nitrogen atom to which they are attached, form a heterocyclic ring with 5 to 7 members in its ring system; and
  $R_5$ and $R_6$ are same or different and indicate hydrogen, halogen, an alkyl group, and an alkoxy group, both with 1 to 3 carbon atoms in the alkyl group, or one of the substituents $R_5$ and $R_6$ being a trifluoro methyl group or a nitro group, while the other one of the substituents $R_5$ and $R_6$ is hydrogen.

The present invention comprises also the acid addition salts of said compounds and more particularly the pharmaceutically acceptable and therapeutically useful acid addition salts.

The low-molecular alkyl substituents $R_1$, $R_3$, and $R_4$ can be straight-chain or branched alkyl groups with 1 to 4 carbon atoms, such as methyl, ethyl, propyl, n-butyl, 1-methyl propyl,2-methyl propyl, and tertiary butyl. Especially preferred substituents are methyl, ethyl, propyl, isopropyl, and tertiary butyl.

If $R_1$ is a phenyl substituted alkyl group, the preferred phenyl substituted alkyl substituents are benzyl and phenyl ethyl.

The most suitable alkyl groups of the mono- or dialkyl amino carbonyl substituents $R_2$ are the above mentioned alkyl groups and preferably methyl, ethyl, propyl, and isopropyl.

The substituent A can be a straight-chain or branched alkylene group with 2 to 5 carbon atoms such as ethylene, propylene, isopropylene, n-butylene, isobutylene, tertiary butylene and, in addition thereto, also pentylene, neopentylene, or isopentylene.

The halogen atoms of the substituents $R_5$ and $R_6$ can be fluorine, chlorine, bromine, and/or iodine and more particularly chlorine and bromine.

Suitable alkyl or alkoxy substituents $R_5$ and $R_6$ are the alkyl or alkoxy groups with methyl, ethyl, n-propyl, or isopropyl. The methyl group is the preferred substituent when both substituents $R_5$ and $R_6$ are alkyl groups.

The cyclic group

can be a pyrrolidine, piperidine, or azacycloheptane ring.

Useful pharmaceutically compatible acid addition salts of the amino alkyl indole compounds of Formula I are not only the hydrochlorides, hydrobromides, hydrogen sulfates, nitrates, or phosphates, but also salts with organic acids such as cyclohexyl amino sulfonic acid, maleic acid, toluene-4-sulfonic acid, or amido sulfonic acid.

The new amino alkyl indole compounds of Formula I and their acid addition salts are prepared by reacting an alkali metal salt of an indole compound of Formula II

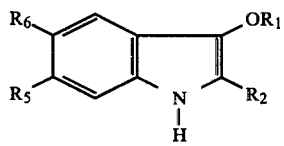

in which
  $R_5$ and $R_6$ are the same substituents as in the compound of Formul I;
  $R_1$ is an alkyl group which may be substituted by a phenyl group, or an acetyl group, and
  $R_2$ is an alkoxy carbonyl group or the cyano group, said alkyl and alkoxy groups having 1 to 4 carbon atoms,
in an inert solvent according to the following process and its variations:

Process (a)

The starting material of Formula II is reacted first with a dihalogeno alkane compound of Formula III $$X_1-A-X_2 \qquad \text{III.}$$

in which
  A is the same group as designated with respect to the compound of Formula I, while
  $X_1$ and $X_2$ are the same or different halogen atoms and preferably chlorine or bromine.
The resulting reaction product is then reacted with an amine of Formula IV

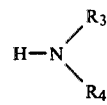

in which
  $R_3$ and $R_4$ are the same substituents as designated with respect to the compound of Formula I.

According to another embodiment of the present invention the substituted indole compound of Formula II is reacted with a halogeno alkyl amine compound of Formula V

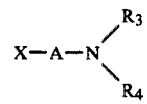

in which
  A is the same substituent as designated with respect to the compound of Formula I, and
  $R_3$ and $R_4$ are also the same substituents, with the exception of hydrogen, as designated with respect to the compound of Formula I, while
  X indicates halogen and preferably chlorine or bromine.

When proceeding in this manner according to both methods, there are obtained amino alkyl indole compounds of Formula Ia

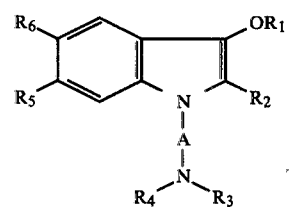

in which the substituents
  A, $R_3$, $R_4$, $R_5$, and $R_6$ are the same substituents as designated hereinabove, while the substituent
  $R_1$ is an alkyl group which may be substituted by a phenyl group or the acetyl group, and the substituent
  $R_2$ is an alkoxy carbonyl group or the cyano group.

Process (b)

If desired, the cyano group or the alkoxy carbonyl group $R_2$ is converted into the hydroxy carbonyl group $R_2$.

Process (c)

According to another embodiment of the present invention the cyano group, the alkoxy carbonyl group, or the hydroxy carbonyl group $R_2$ are converted into the amino carbonyl group, the mono-alkyl amino carbonyl group, or the dialkyl amino carbonyl group $R_2$.

Process (d)

If desired, the acetyl group $R_1$ of the compounds obtained according to the above described processes (a) or (c) can be split off hydrolytically to yield the corresponding 3-hydroxy indole compound.

Process (e)

Another variation of the process according to the present invention consists in hydrogenolytically splitting off the phenyl substituted alkoxy group $OR_1$, such as the benzyloxy group of indole compounds obtained according to the process (a) or (c) hereinabove so as to obtain the corresponding 3-hydroxy indole compounds of Formula I.

Process (f)

According to another variation of the present invention, the 3-hydroxy indole compounds can be obtained by hydrolytically splitting off the alkyl group from the corresponding alkoxy group $OR_1$ of the compounds obtained according to the processes (a) or (c) described hereinabove.

Process (g)

The basic amino alkyl indole compounds of Formula I obtained according to the above described processes are isolated and are converted, if desired, into their acid addition salts.

The indole compounds of Formula II which serve as starting materials for the production of the amino alkyl indole compounds of Formula I are known. They can be obtained, for instance, by basic cyclisation of the corresponding N-alkoxy carbonyl methyl anthranilic acid esters followed by etherification of the resulting enolate as this is described, for instance, in French Pat. No. 1,503,908. Said Patent discloses these indole compounds as intermediates in the production of other compounds.

The 3-hydroxy indole derivatives of Formula II, used as starting materials, are provided with a protective group before their reaction. A preferred protective group is, for instance, the 3-acetoxy group. Thus the 3-acetoxy compounds are used as starting materials.

The Process (a), as described hereinabove, according to which the amino alkyl group is attached to the indole nitrogen atom in 1-position of the respective starting material of Formula II represents an alkylation process which is known per se. Advantageously an alkali metal salt of an indole compound of Formula II is first produced by suitably carrying out the reaction in an inert solvent such as dimethyl formamide, sulfolane, 1,4-dioxane, dimethyl sulfoxide, or toluene, at a temperature between −20° C. and room temperature and preferably at a temperature between −10° C. and +10° C. Suitable bases, as used in this reaction, are, for instance, alkali metal alcoholates, such as sodium methylate, sodium ethylate, potassium tertiary butylate, or alkali metal amides, such as sodium amide, lithium di-isopropylamide, or alkali metal hydrides, such as sodium hydride.

The amino alkyl group can then be introduced into the alkali metal indole compound either in a two-step process by reacting a solution of the alkali metal indole compound in the above mentioned solvent first with a dihalogeno alkane compound and then with the corresponding amine or, in a one-step process, by directly reacting a solution of the alkali metal indole compound with a halogeno alkyl amine.

In the first mentioned process the dihalogeno alkane compound of Formula III is added to the solution of the alkali metal indole compound and the mixture is preferably heated at a temperature between about 60° C. and about 90° C. under atmospheric or increased pressure. Under such reaction conditions there is produced the N-(halogeno alkyl) indole derivative of the Formula VI

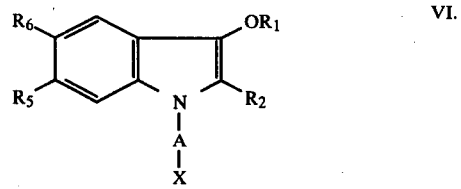

in which the substituents $R_1$, $R_2$, $R_5$, $R_6$, and A indicate the same groups as given hereinabove with respect to the compound of Formula I, while the substituent X is halogen and preferably chlorine or bromine.

When using as the one reactant a dihalogeno alkane compound of Formula III with different halogen atoms, the substituent X indicates the halogen atom which tends to react more slowly than the other halogen atom of the dihalogeno alkane. The halogen atom X is preferably chlorine.

The N-(halogeno alkyl) indole derivative obtained in this manner can be isolated from the reaction mixture and, if desired, recrystallized before it is reacted with ammonia or the respective alkyl amine. The reaction with the amine compound of Formula IV can also be carried out in an inert solvent, such as dimethyl formamide, sulfolane, tetrahydrofurane, 1,4-dioxane, toluene, dimethyl sulfoxide, or mixtures of said solvents, at atmospheric or increased pressure. The reaction temperature is between room temperature and the boiling point of the solvent employed, and preferably between 40° C. and 60° C. As acid binding agents there can be used alkali metal or alkaline earth metal carbonates, such as sodium carbonate, potassium carbonate, or calcium carbonate, furthermore tertiary amines, such as triethylamine or pyridine. It is also possible to use an excess of the amine reactants of Formula IV. These reactants can also be used as solvents by employing an excess thereof.

When proceeding according to the one-step process described hereinabove, the halogeno alkyl amine of Formula V is added to the solution of the alkali metal salt of the indole derivative of Formula II. The mixture of the reaactants is then reacted at a temperature between room temperature and the boiling point of the solvent used, at atmospheric or increased pressure. The preferred reaction temperatures are between 60° C. and 90° C.

To produce N-amino alkyl indole compounds of Formula I in which the substituent $R_2$ is a hydroxy carbonyl group, there can be subjected to a hydrolytic cleavage process the corresponding indole compounds of Formula I in which the substituent $R_2$ is the cyano group or an alkoxy carbonyl group. Preferably the alkoxy carbonyl compounds are hydrolyzed, i.e. the alkyl esters are hydrolyzed, i.e. de-esterified, in a manner known per se, in an acid or alkaline medium. Suitable acid hydrolysis is effected by means of dilute hydrochloric acid or dilute sulfuric acid at a temperature between 60° C. and 100° C. Suitable solvents are lower alcohols, tetrahydrofurane, 1,4-dioxane, as such or in mixture with water. Basic hydrolysis is preferably carried out by means of aqueous alkali metal hydroxide or carbonate solutions, preferably with aqueous sodium hydroxide, potassium hydroxide, sodium carbonate, or potassium carbonate solutions at a temperature between 15° C. and 100° C. and most advantageously at a temperature between 50° C. and 70° C. Alkaline hydrolysis yields the corresponding alkali metal salts of the resulting indole carboxylic acids. Said alkali metal salts can be converted into the free carboxylic acid compounds of Formula I by acidifying with a mineral acid, such as hydrochloric acid or sulfuric acid, or also with an organic acid, such as acetic acid.

In order to produce N-amino alkyl indole compounds of Formula I in which the substituent $R_2$ is an amino carbonyl group, the amino group of which may be substituted, there may be used as starting material indole compounds of Formula I in which the substituent $R_2$ is a cyano, alkoxy carbonyl, or hydroxy carbonyl group. The respective cyano compounds can be converted into the corresponding amides of Formula I, for instance, by reaction with a mineral acid or with an alkaline agent, such as sodium or potassium hydroxide in solution in a suitable solvent. If desired, hydrogen peroxide may be added to the reaction mixture.

The alkoxy carbonyl compounds of Formula I can be converted into the corresponding amino carbonyl indole compounds of Formula I by ammonolysis or, respectively, aminolysis in a manner known per se, i.e. by reaction with ammonia or a primary or secondary alkyl amine under atmospheric or increased pressure.

Especially advantageous is the conversion of the hydroxy carbonyl group $R_2$ of the indole compounds of Formula I into the amide group which may be substituted. This conversion of a carboxylic acid function into a carboxylic acid amide function can be effected in a manner known per se directly by reaction of the free carboxylic acid with ammonia or a primary or secondary alkylamine.

It can be of advantage to carry out said reaction in two steps. For this purpose the respective free carboxylic acid is first converted into a derivative which is capable to yield in a second reaction step the desired carboxylic acid amide. Such a reactive intermediate derivative is, for instance, the corresponding carboxylic acid halogenide and especially the carboxylic acid chloride, or a reactive carboxylic acid anhydride, or a carboxylic acid imidazolide. Said intermediate compound may also be a condensation product of the carboxylic acid with N,N'-dicyclohexyl carbodi-imide. The resulting carboxylic acid derivative is then converted in situ into the carboxylic acid amide by reaction with ammonia or an alkylamine.

In order to produce the respective carboxylic acid anhydride, the free carboxylic acid is reacted most suitably with a chloro formic acid alkyl ester, for instance, with the ethyl ester. The temperature during said reaction is, for instance, between −5° C. and room temperature. An inert solvent, for instance, chloroform, toluene, tetrahydrofurane, or dimethyl formamide may serve as reaction medium. The conversion of the carboxylic acid into the corresponding imidazolide is carried out, for instance, by reaction with carbonyl di-imidazole in an inert solvent such as tetrahydrofurane or chloroform at a temperature between −10° C. and room temperature. The condensation of the carboxylic acid with N,N'-dicyclohexyl carbodi-imide can be carried out at similar temperatures in an inert organic solvent such as methylene chloride, 1,4-dioxane, toluene, or mixtures thereof.

The reaction of the above described carboxylic acid derivatives with ammonia or a primary or secondary alkyl amine is preferably carried out at a temperature between −5° C. and room temperature in a solvent, such as water, chloroform, toluene, tetrahydrofurane, dimethyl formamide, or mixtures thereof. It can be of advantage to use an excess of the amine reactant as acid binding agent or to carry out the reaction in the presence of other acid binding agents, such as, for instance, potassium carbonate, sodium carbonate, sodium hydroxide, potassium hydroxide, tri-ethyl amine, or pyridine. When using an excess of the respective amines, they can additionally serve as solvents.

The compounds of Formula I in which $R_1$ is hydrogen and $R_2$ is a cyano group, an alkoxy carbonyl group, or an amino carbonyl group in which the amino group may be substituted, and $R_3$, $R_4$, $R_5$, and $R_6$ indicate the same substituents as given hereinabove for the compounds of Formula I, can be obtained from the compounds prepared according to the processes described hereinabove under (a) or (c) by splitting off the acetyl group which serves as protective group. To achieve this result, there is reacted preferably the enol acetate of the Formula I in a solvent such as water, methanol, ethanol, acetone, tetrahydrofurane, 1,4-dioxane, or mixtures thereof with an alkali metal carbonate or an alkaline earth metal carbonate, such as sodium carbonate, potassium carbonate, or also with ammonium carbonate, at a temperature between 0° C. and 40° C.

Preparation of the 3-hydroxy derivatives of the indole compounds of Formula I can be achieved by hydrogenation of the corresponding benzyl ethers of the indole compounds of Formula I in an inert organic solvent, such as methanol, ethanol, ethyl acetate, or 1,4-dioxane, if desired, in the presence of a catalyst, such as, for instance, palladium deposited on charcoal, under atmospheric pressure or under increased pressure and at a temperature between room temperature and 150° C., preferably at a temperature between 40° C. and 80° C.

The preparation of the enol compounds, however, can also be effected by reacting the corresponding 3-alkoxy indole compounds of Formula I with a non-oxidizing mineral acid in an organic solvent, for instance, with concentrated hydrochloric acid in methanol, ethanol, or 1,4-dioxane at a temperature near the boiling point of the reaction mixture or by boiling under reflux.

The novel indole compounds according to the present invention and their acid addition salts—as far as they are not important intermediate products—exhibit valuable therapeutic properties. More particularly, they have a pronounced effect upon the motility disturbances of the gastro-intestinal tract. These properties and effects will be described more in detail hereinafter.

DESCRIPTION OF THE PREFERRED EMBODIMENTS

The following examples serve to illustrate the present invention and more particularly the processes of producing the novel amino alkyl indole compounds of Formula I given hereinabove, without, however, being limited thereto.

EXAMPLE 1

20.5 g. of 2-methoxy carbonyl-3-methoxy indole are dissolved in 100 ml. of dimethyl formamide. 3 g. of 80% sodium hydride are added portion by portion thereto at 0° C., while stirring. After heating the mixture to room temperature, 20 g. of 1-bromo-3-chloro propane are added thereto. The reaction mixture is heated to 80° C. for 12 hours whereupon the solvent is drawn off. The reaction mixture is worked up in the usual manner by means of ethyl acetate and water. The resulting crude reaction product is subjected to a distillation in a tubular distillation apparatus with bulbar enlargements. 24.7 g. of 1-(γ-chloro propyl)-2-methoxy carbonyl-3-methoxy indole are obtained in the form of an oil. Said compound is dissolved in 100 ml. of dimethyl formamide. The solution is then heated with 20 g. of diethylamine to 60° C. for 5 hours. After drawing off the solvent and adding 10% hydrochloric acid to the residue, the mixture is extracted with ethyl acetate. Thereupon the aqueous phase is rendered alkaline by the addition of a sodium carbonate solution and the mixture is extracted with ethyl acetate. The organic phase is dried over sodium sulfate, filtered, and the filtrate is evaporated to dryness under reduced pressure. 25.8 g. of 1-(γ-diethyl amino propyl)-2-methoxy carbonyl-3-methoxy indole are obtained as an oily residue. The yield is 81% of the theoretical yield. Said compound can be converted into its crystalline maleinate with a melting point of 110°-112° C.

The 1-(γ-chloro propyl)-2-methoxy carbonyl-3-methoxy indole can be reacted with methylamine or ammonia under corresponding reaction conditions. The resulting amino alkyl indole compounds can be converted, if desired, on subsequent reaction with an acid, into the respective acid addition salts. In this manner there were obtained the following compounds:

1-(γ-methylamino propyl)-2-methoxy carbonyl-3-methoxy indole as an oil.

Infrared spectrum: 1695 cm.$^{-1}$, 3300 cm.$^{-1}$ (carbonyl/NH).

1-(γ-amino propyl)-2-methoxy carbonyl-3-methoxy indole hydrochloride. Melting point: 184°-186° C.

EXAMPLE 2

When following the procedure as described in Example 1, there are obtained from 20.5 g. of 2-methoxy carbonyl-3-methoxy indole dissolved in 100 ml. of dimethyl formamide, with 3 g. of 80% sodium hydride and 22 g. of 1-bromo-4-chloro butane, 25.1 g. of 1-(δ-chloro butyl)-2-methoxy carbonyl-3-methoxy indole in the form of an oil. A solution of said compound in 100 ml. of dimethyl formamide is reacted with dimethyl amine at 50° C. The resulting 1-(δ-dimethyl amino butyl)-2-methoxy carbonyl-3-methoxy indole is converted into its acid addition salt by reaction with toluene-4-sulfonic acid, 29,4 g. of crystalline 1-(δ-dimethyl amino butyl)-2-methoxy carbonyl-3-methoxy indole toluene-4-sulfonate with the melting point of 133°-135° C. are obtained. The yield is 62% of the theoretical yield.

EXAMPLE 3

20.5 g. of 2-methoxy carbonyl-3-methoxy indole are dissolved in 60 ml. of dimethyl formamide. 3 g. of 80% sodium hydride are added portion by portion thereto while stirring and cooling the solution with ice. 15 minutes thereafter there are added 12 g. of 1-dimethyl amino-2-chloro ethane. The reaction mixture is then heated to 60° C. for 2 hours and subsequently evaporated to dryness under reduced pressure. The residue is acidified by the addition of 10% hydrochloric acid and is extracted with ethyl acetate. Thereupon the aqueous phase is rendered alkaline by the addition of a sodium carbonate solution and is extracted with ethyl acetate. The organic phase is dried by means of sodium sulfate, filtered, and evaporated to dryness under reduced pressure. 23.7 g. of 1-(β-dimethyl amino ethyl)-2-methoxy carbonyl-3-methoxy indole are obtained in the form of an oil. The yield is 86% of the theoretical yield.

In order to produce acid addition salts of this indole compound, the oil is dissolved in 100 ml. of methanol and hydrogen chloride in the gaseous state is introduced into the solution. The precipitated acid addition salt is filtered off by suction, washed with methanol and ether, and dried. The monohydrochloride of the 1-(β-dimethyl amino ethyl)-2-methoxy carbonyl-3-methoxy indole which melts at 202°-203° C. (with decomposition) is obtained.

EXAMPLE 4

When proceeding as described in Examples 1 to 3 and starting with the alkali metal salts of the respective indole derivatives, there are obtained the following compounds:

| | Melting Point °C. |
|---|---|
| 1-(β-Diethyl amino ethyl)-2-ethoxy carbonyl-3-ethoxy indole maleinate | 110-112 |
| 1-(β-dimethyl amino ethyl)-2-isopropyloxy carbonyl-3-methoxy indole; IR: 1685 cm.$^{-1}$ (Carbonyl) | oil |
| 1-(β-dimethyl amino ethyl)-2-methoxy carbonyl-3-isopropyloxy-5-methyl-indole hydrochloride | 206-208 |
| 1-(β-dimethyl amino ethyl)-2-methoxy carbonyl-3-methoxy-6-methyl indole hydrochloride | 198-200 |
| 1-(β-dimethyl amino ethyl)-2-methoxy carbonyl-3-ethoxy-5-chloro indole hydrochloride | 175-177 |
| 1-(β-dimethyl amino ethyl)-2-methoxy carbonyl-3-benzyloxy-5-chloro indole toluene-4-sulfonate | 175-177 |
| 1-(β-dimethyl amino ethyl)-2-ethoxy carbonyl-3-ethoxy-6-chloro indole toluene-4-sulfonate | 152-154 |
| 1-(β-dimethyl amino ethyl)-2-methoxy carbonyl-3-methoxy-5-bromo indole hydrochloride | 190-191 |
| 1-(β-dimethyl amino ethyl)-2-methoxy carbonyl-3-methoxy-5-nitro indole; IR: 1690 cm.$^{-1}$ (C=O) | oil |
| 1-(β-dimethyl amino ethyl)-2-methoxy carbonyl-3,5-dimethoxy indole hydrochloride | 182-184 |
| 1-(β-dimethyl amino ethyl)-2-methoxy carbonyl-3,5,6-trimethoxy indole hydrochloride | 203-204 |
| 1-(β-dimethyl amino ethyl)-2-methoxy carbonyl-3-methoxy-5-bromo-6-methyl indole hydrochloride | 200-202 |
| 1-(β-dimethyl amino ethyl)-2-cyano-3-methoxy indole: IR: 2230 cm.$^{-1}$ (nitrile) | oil |
| 1-(γ-dimethyl amino propyl)-2-methoxy carbonyl-3-methoxy indole hydrochloride | 154-155 |
| 1-(β-dimethyl amino propyl)-2-methoxy carbonyl-3-methoxy indole hydrochloride | 186-188 |
| 1-(γ-di-isopropyl amino propyl)-2-methoxy carbonyl-3-methoxy indole; IR: 1700 cm.$^{-1}$ (carbonyl) | oil |
| 1-(γ-pyrrolidino propyl)-2-methoxy carbonyl-3-methoxy indole; IR: 1700 cm.$^{-1}$ (carbonyl) | oil |
| 1-(γ-piperidino propyl)-2-methoxy carbonyl-3-methoxy indole maleinate | 104-106 |
| 1-(γ-isopropyl amino propyl)-2-methoxy carbonyl-3-methoxy indole hydrochloride | 148-149. |

EXAMPLE 5

A solution of 23.3 g. of 2-methoxy carbonyl-3-acetoxy indole in dimethyl formamide is reacted in accordance with the procedure described in Example 2 with 3 g. of sodium hydride and, thereafter, with 1-dimethyl amino-2-chloro ethane so as to yield 1-(β-dimethyl amino ethyl)-2-methoxy carbonyl-3-acetoxy indole of the melting point 165°-167° C. Said compound is dissolved in 150 ml. of methanol. A solution of 10 g. of sodium carbonate in 100 ml. of water is added thereto and the mixture is stirred at room temperature for one hour. Thereupon, the pH-value of the reaction mixture is adjusted to a pH of 8.0 by the addition of dilute hydrochloric acid, the solvent is largely drawn off, and the residue is worked up in the usual manner with ethyl acetate and water. The resulting 1-(β-dimethyl amino ethyl)-2-methoxy carbonyl-3-hydroxy indole is converted into its maleinate which, on recrystallization from ethyl acetate and ether is obtained with a melting point of 156°–158° C. The yield is 26.8 g. corresponding to 71% of the theoretical yield.

EXAMPLE 6

2.0 g. of 1-(β-dimethyl amino ethyl)-2-methoxy carbonyl-3-benzyloxy-5-chloro indole are dissolved in 50 ml. of ethyl acetate and are hydrogenated with the addition of 2.0 g. of a palladium catalyst (5% of palladium deposited on charcoal) at room temperature and under atmospheric pressure. After 2 hours the catalyst is separated by filtration and the remaining reaction solution is concentrated by evaporation. 1.5 g. of 1-(β-dimethyl amino ethyl)-2-methoxy carbonyl-3-hydroxy-5-chloro indole are obtained in the form of a slightly yellowish oil.

Infrared spectrum: 1710 cm.$^{-1}$ (carbonyl), 3300 cm.$^{-1}$ (hydroxyl).

EXAMPLE 7

3.5 g. of 1-(γ-diethyl amino propyl)-2-ethoxy carbonyl-3-ethoxy indole are dissolved in 50 ml. of ethanol. The resulting solution is boiled under reflux with 2.5 ml. of concentrated hydrochloric acid for 12 hours. Thereafter, the solvent is largely drawn off, the residue is rendered alkaline by the addition of a sodium carbonate solution while at room temperature, and is worked up by means of dichloro methane in the usual manner. The resulting 1-(γ-diethyl amino propyl)-2-ethoxy carbonyl-3-hydroxy indole is obtained in oily form with a yield of 2.7 g. corresponding to 85% of the theoretical yield.

Infrared spectrum: 1715 cm.$^{-1}$ (carbonyl), 3280 cm.$^{-1}$ (hydroxyl).

EXAMPLE 8

27.6 g. of 1-(β-dimethyl amino ethyl)-2-methoxy carbonyl-3-methoxy indole are dissolved in 150 ml. of methanol. A solution of 4.4 g. of sodium hydroxide in 40 ml. of water is added thereto. The mixture is boiled under reflux for one hour. Thereafter, the reaction mixture is adjusted to a pH of 7.0 by the addition of acetic acid and is concentrated by evaporation under reduced pressure. The resulting residue is dissolved in water. The aqueous solution is saturated with ammonium sulfate and is extracted with ethyl acetate. The organic phase is dried, filtered, and evaporated to dryness. The residue is recrystallized from methanol. 24.7 g. of 1-(β-dimethyl amino ethyl)-2-hydroxy carbonyl-3-methoxy indole with a melting point of 188–190. C. are obtained. Yield: 94% of the theoretical yield.

By proceeding according to the process as described above, there are obtained the following indole compounds from the respective starting materials:

1-(γ-Dimethyl amino propyl)-2-hydroxy carbonyl-3-methoxy indole, oil
1-(β-dimethyl amino ethyl)-2-hydroxy carbonyl-3-ethoxy indole, Melting point: 160°–165° C.
1-(β-dimethyl amino ethyl)-2-hydroxy carbonyl-3-benzyloxy indole, oil
1-(β-dimethyl amino ethyl)-2-hydroxy carbonyl-3-methoxy-5-chloro indole, oil
1-(β-dimethyl amino ethyl)-2-hydroxy carbonyl-3-methoxy-6-chloro indole, oil
1-(β-dimethyl amino ethyl)-2-hydroxy carbonyl-3-methoxy-5-methyl indole, Melting point: 159°–163° C.
1-(β-dimethyl amino ethyl)-2-hydroxy carbonyl-3-methoxy-5-methoxy indole, oil
1-(β-dimethyl amino ethyl)-2-hydroxy carbonyl-3-methoxy-5,6-dimethoxy indole, oil
1-(β-diethyl amino ethyl)-2-hydroxy carbonyl-3-methoxy indole, oil
1-(β-methyl amino ethyl)-2-hydroxy carbonyl-3-methoxy indole oil.

EXAMPLE 9

2.6 g. of 1-(β-dimethyl amino ethyl)-2-hydroxy carbonyl-3-methoxy indole are dissolved in 50 ml. of dichloro methane and 1.0 g. of tri-ethyl amine. 10 ml. of concentrated aqueous ammonia are added to the resulting solution. The mixture is cooled to 0° C. 1.1 g. of chloro formic acid ethyl ester are added thereto while stirring. The temperature of the reaction mixture is allowed to rise to room temperature whereafter the mixture is worked up with dichloro methane and water in the usual manner. The resulting 1-(β-dimethyl amino ethyl)-2-amino carbonyl-3-methoxy indole is obtained in crystalline form with the melting point of 113°–115° C. by recrystallization from methylene chloride and ether. Its melting point is 113°–115° C. The yield amounts to 1.7 g. corresponding to 65% of the theoretical yield.

When proceeding as described hereinabove and reacting 1-(β-dimethyl amino ethyl)-2-hydroxy carbonyl-3-methoxy indole with methylamine, there is obtained the 1-(β-dimethyl amino ethyl)-2-methyl amino carbonyl-3-methoxy indole with a melting point of 175° C. (with decomposition).

EXAMPLE 10

2.6 g. of 1-(β-dimethyl amino ethyl)-2-hydroxy carbonyl-3-methoxy indole and 2.3 g. of dicyclohexyl carbodi-imide are dissolved in 50 ml. of dichloro methane. The solution is cooled to 0° C. After allowing the mixture to stand for 30 minutes, 5 ml. of diethylamine are added thereto, while stirring. The resulting reaction mixture is then heated to room temperature, is concentrated by evaporation, and is worked up in the usual manner by means of ethyl acetate and water. The residue is purified by chromatography on aluminum oxide by means of cyclohexane and ethyl acetate. 1.7 g. of 1-(β-dimethyl amino ethyl)-2-diethylamino carbonyl-3-methoxy indole are obtained in the form of a colorless oil.

Infrared spectrum: 1620 cm.$^{-1}$ (carbonyl).

EXAMPLE 11

2.9 g. of 1-(β-dimethyl amino ethyl)-2-methoxy carbonyl-3-methoxy-5-methyl indole are heated under reflux in 65 ml. of di-isopropyl amine for 5 hours. The unreacted solvent is then drawn off and the remaining oil is purified by subjecting it to column chromatography on silicagel and elution with ether and petroleum ether. The resulting 1-(β-dimethyl amino ethyl)-2-di-isopropyl amino carbonyl-3-methoxy-5-methyl indole is obtained in the form of a colorless oil. Yield: 1.7 g. corresponding to 47% of the theoretical yield.

Infrared spectrum: 1615 cm.$^{-1}$ (carbonyl).

In the same manner as described hereinabove in Examples 9 to 11 and by using the respective starting materials there can be obtained the following compounds:

1-(β-Dimethyl amino ethyl)-2-diethyl amino carbonyl-3-methoxy-6-methyl indole,
1-(β-dimethyl amino ethyl)-2-diethyl amino carbonyl-3-ethoxy-5-chloro indole,
1-(β-dimethyl amino ethyl)-2-diethyl amino carbonyl-3-isopropyloxy-5-methyl indole,
1-(β-dimethyl amino ethyl)-2-diethyl amino carbonyl-3-benzyloxy-5-chloro indole,
1-(γ-isopropyl amino propyl)-2-diethyl amino carbonyl-3-methoxy indole,
1-(δ-dimethyl amino butyl)-2-diethyl amino carbonyl-3-methoxy indole,
1-(γ-N-piperidino propyl)-2-diethyl amino carbonyl-3-methoxy indole.

Of course, other N-amino alkyl indole compounds of Formula I as given hereinabove can be prepared by using the respective starting materials and proceeding according to the aforesaid examples.

As stated hereinabove, it is an important feature of the present invention to provide the medical profession with novel and highly effective therapeutic agents for restoring the physiological motility and unimpeded passage of food through the stomach.

Surprisingly it was found that the N-amino alkyl indole compounds of Formula I, according to the present invention, have such an effect. The peristaltic wave-like movements of the stomach are intensified under their action as can be shown in animal experiments. Due thereto the frequency of the movements decreases in favor of more vigorous, more deeply constricting, and contracting wave-like movements. The effects demonstrated in these animal experiments allow us to assume that a considerable improvement of the discharging ability of the stomach is achieved.

DESCRIPTION OF THE PHARMACOLOGICAL TEST METHODS

1. Determination of the acute toxicity

The acute seven-day toxicity is determined by intraperitoneal administration of a single dose of the respective compound to a fasting white NMRI mouse. The $LD_{50}$-values are calculated via EDV by a probit analysis as described in the book "Grundbegriffe der Biometrie" (Basic biometrical definitions) by L. Cavalli-Sforza, page 153 et seq., published by Gustav Fischer Verlag, Stuttgart, 1964.

2. Testing of the gastric peristalsis

To determine the functioning of the gastric peristalsis, rats weighing about 200 g. are narcotized by means of ketamine hydrochloride and xylazine. A catheter is introduced into the Vena jugularis of the narcotized rats and a tracheal catheter into their trachea. A stomach probe is inserted into their stomach and tied thereto. Said probe is connected via a three-way cock with a Statham pressure imparting device (P 23 DB). The stomach is sealed off by a ligature at the pylorus and at the cardia. The stomach is filled with 3 ml. of an 0.9% aqueous sodium chloride solution. The pressure waves produced by the stomach are continuously registered by a suitable recording device such as by a Watanabe Multicorder (MC 641). In order to determine the effect of the compounds to be tested, they are dissolved in physiological sodium chloride solution or are suspended in Tylose MH 50 solution. Said solutions or suspensions are administered intraperitoneally to the rats in a dosis of 20 mg./kg. The amplitudes and frequencies of the pressure wave-like movements of the stomach as they occur before and after administration of the compound to be tested, are compared.

Evaluation of the test results show that a considerable increase in the amplitudes takes place shortly after administration of the compounds according to the present invention. This effect in combination with a pronounced decrease in the frequencies of varying magnitude results in an improved food passage through the stomach.

The following N-amino alkyl indole compounds were tested according to these methods:

(A) 1-(β-Dimethyl amino ethyl)-2-methoxy carbonyl-3-methoxy-indole hydrochloride,
(B) 1-(β-dimethyl amino ethyl)-2-methoxy carbonyl-3-methoxy-6-methyl indole hydrochloride,
(C) 1-(β-dimethyl amino ethyl)-2-methoxy carbonyl-3-ethoxy-5-chloro indole hydrochloride,
(D) 1-(β-dimethyl amino ethyl)-2-methoxy carbonyl-3-isopropyloxy-5-methyl indole hydrochloride,
(E) 1-(β-dimethyl amino ethyl)-2-methoxy carbonyl-3-benzyloxy-5-chloro indole toluene-4-sulfonate,
(F) 1-(β-dimethyl amino ethyl)-2-ethoxy carbonyl-3-ethoxy-6-chloro indole toluene-4-sulfonate,
(G) 1-(γ-isopropyl amino propyl)-2-methoxy carbonyl-3-methoxy indole hydrochloride,
(H) 1-(δ-dimethyl amino butyl)-2-methoxy carbonyl-3-methoxy indole toluene-4-sulfonate,
(I) 1-(γ-N-piperidino propyl)-2-methoxy carbonyl-3-methoxy indole maleinate,
(K) 1-(β-dimethyl amino ethyl)-2-hydroxy carbonyl-3-methoxy indole,
(L) 1-(β-dimethyl amino ethyl)-2-amino carbonyl-3-methoxy indole,
(M) 1-(β-dimethyl amino ethyl)-2-methylamino carbonyl-3-methoxy indole.

The following Table shows the results obtained on determining amplitudes and frequencies of gastric peristalsis determined as described hereinabove:

TABLE

| | Measurements of the gastric pressure. | | |
|---|---|---|---|
| Compound tested | Factor of the increase in amplitude | Frequency decrease in % | $LD_{50}$ i.p. mg./kg. |
| (A) | 6.2 | 3.3 | 171 |
| (B) | 22.7 | 7.0 | 68 |
| (C) | 1.4 | 9.0 | 141 |
| (D) | 6.9 | 19.0 | 137 |
| (E) | 0.6 | −2.0 | 283 |
| (F) | 10.9 | 5.0 | 226 |
| (G) | 8.3 | 29.0 | 91 |
| (H) | 3.5 | 11.0 | 164 |
| (I) | 8.6 | 15.0 | 141 |
| (K) | 3.6 | 21.0 | 967 |
| (L) | 13.9 | 28.0 | 68 |
| (M) | 21.4 | 13.0 | 68 |

The preceding Table contains the measured values.

The results given in said Table clearly show that even small doses of the compounds according to the present invention and their acid addition salts cause a significant intensification of the peristaltic wave-like movements of the stomach. At the same time, the high activity and the low toxicity of the tested compounds indicate that they are well compatible. A further advantage of the compounds tested is the observed rapid onset of their physiological action.

The pharmacologically observed effects clearly indicate that the compounds according to the present invention are capable of overcoming or at least alleviating disorders and disturbances of the gastrointestinal functions of the human body, such as, for instance, stenoses of the pylorus, duodeno-gastric reflux as well as atonic conditions. A favorable therapeutic effect can furthermore be expected in functional disorders which cause pain in the upper abdominal region of the body, nausea, a sense of fullness, and other unpleasant symptoms, such as the disagreeable symptoms encountered in the case of an ulcus ventriculi and ulcus duodeni, gastritis and nervous irritation of the stomach. Furthermore, an increased passage of an X-ray contrast agent through the stomach is achieved by administration of the compounds according to the present invention. This effect is highly desirable in the X-ray diagnosis of the gastro-intestinal tract.

Suitable pharmaceutical preparations according to the present invention contain, as effective agents, the N-amino alkyl indole compounds of Formula I or their pharmacologically compatible acid addition salts in combination with conventional pharmaceutically acceptable excipients, such as carrier materials and/or diluents. The resulting pharmaceutical preparations can be administered orally or parenterally. Suitable preparations are in the form of tablets, capsules, lozenges, sirups, dry powders, injectable or infusible solutions or suspensions. They can also be prepared and administered in the form of suppositories. The preferred preparations are those which can be orally administered.

The dosage to be administered of the pharmaceutical compounds according to the present invention is dependent on various factors, such as the kind and the seriousness of the disease or the compound to be administered. In general, a single dose of between 1 mg. and 50 mg. and preferably between 2 mg. to 20 mg., administered orally, is sufficient to achieve satisfactory results.

The following example illustrates the preparation of an orally administrable composition without, however, being limited thereto.

EXAMPLE 12

Capsules containing 1-(β-dimethyl amino ethyl)-2-methoxy carbonyl-3-methoxy indole hydrochloride as active agent.

Each capsule contains an intimate mixture of the following ingredients:

| | |
|---|---|
| Active indole compound | 10 mg. |
| Lactose | 65 mg. |
| Dried corn starch | 40 mg. |
| Soluble starch | 4 mg. |
| Magnesium stearate | 1 mg. |
| Total content of each capsule | 120 mg. |

Of course, many changes and variations in the process of producing the compounds of Formula I according to the present invention and of their acid addition salts, in the reactants and solvents used, in the reaction conditions, temperature, pressure, and duration, in the manner of working up the reaction mixture and of isolating and purifying the resulting reaction products, in the preparation of pharmaceutical compositions containing said N-amino alkyl indole compounds and their acid addition salts, in the method of administering said pharmaceutical compositions for the treatment of motility disorders of the gastro-intestinal tract, and the like may be made by those skilled in the art in accordance with the principles set forth herein and in the claims annexed hereto.

We claim:
1. An N-amino alkyl indole compound of Formula I

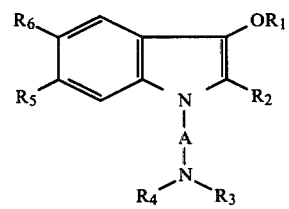

in which
$R_1$ indicates the hydrogen atom, an alkyl group with 1 to 4 carbon atoms, a phenyl substituted alkyl group with 1 to 4 alkyl carbon atoms, or an acetyl group;
$R_2$ indicates the hydroxy carbonyl group, an alkoxy carbonyl group with 1 to 4 alkyl carbon atoms, the cyano group, an amino carbonyl group, or a mono- or di-alkyl amino carbonyl group with 1 to 4 alkyl carbon atoms, with the provise that when $R_2$ is the hydroxy carbonyl group, then $R_1$ must be another substituent than the hydrogen atom;
A indicates an alkylene group with 2 to 5 carbon atoms;
$R_3$ and $R_4$ are the same or different substituents and indicate the hydrogen atom, an alkyl group with 1 to 4 carbon atoms, or $R_3$ and $R_4$ being an alkylene group and forming together with the nitrogen atom to which they are attached, a heterocyclic ring with 5 to 7 ring members; and
$R_5$ and $R_6$ are same or different and indicate the hydrogen atom, a halogen atom, an alkyl group with 1 to 3 carbon atoms, an alkoxy group with 1 to 3 carbon atoms, or one of the substituents $R_5$ and $R_6$ being the trifluoro methyl group or the nitro group while the other one indicates the hydrogen atom;
and the pharmaceutically acceptable acid addition salts of said indole compounds.

2. The indole compound of claim 1, in which
$R_1$ is the methoxy group,
$R_2$ is the methoxy carbonyl group,
A is the ethylene group,
$R_3$ and $R_4$ are methyl groups,
$R_5$ is the hydrogen atom, the methyl group, or the methoxy group, and
$R_6$ is the hydrogen atom, the bromine atom, or the methoxy group,
said compound being a 1-(β-dimethyl amino ethyl)-2-methoxy carbonyl-3-methoxy indole compound substituted in 5-position by the hydrogen atom, the bromine atom, or the methoxy group and in 6-position by the hydrogen atom, the methyl group, or the methoxy group.

3. The indole compound of claim 1, in which
$R_1$ is the methoxy group;
$R_2$ is the methoxy carbonyl group;
A is the ethylene group;
$R_3$ and $R_4$ are methyl groups;
$R_5$ is the hydrogen atom; and
$R_6$ is the nitro group;

said compound being 1-(β-dimethyl amino ethyl)-2-methoxy carbonyl-3-methoxy-5-nitro indole.

4. The indole compound of claim 1, in which
$R_1$ is the ethoxy group, the isopropyloxy group, or the benzyloxy group;
$R_2$ is the methoxy carbonyl group;
A is the ethylene group;
$R_3$ and $R_4$ are methyl groups;
$R_5$ is the hydrogen atom, and
$R_6$ is the chlorine atom or the methyl group;
said compound being 1-(β-dimethyl amino ethyl)-2-methoxy carbonyl indole compound substituted in 3-position by the substituent $R_1$ and in 5-position by the substituent $R_6$ as indicated above.

5. The indole compound of claim 1, in which
$R_1$ is the ethoxy group,
$R_2$ is the ethoxy carbonyl group,
A is the ethylene group,
$R_3$ and $R_4$ are methyl groups,
$R_5$ is the chlorine atom, and
$R_6$ is the hydrogen atom,
said compound being 1-(β-dimethyl amino ethyl)-2-ethoxy carbonyl-3-ethoxy-6-chloro indole.

6. The indole compound of claim 1, in which
$R_1$ is the methoxy group,
$R_2$ is the isopropyloxy carbonyl group,
A is the ethylene group,
$R_3$ and $R_4$ are methyl groups, and
$R_5$ and $R_6$ are hydrogen atoms,
said compound being 1-(β-dimethyl amino ethyl)-2-isopropyloxy carbonyl-3-methoxy indole.

7. The indole compound of claim 1, in which
$R_1$ is the ethoxy group,
$R_2$ is the ethoxy carbonyl group,
A is the ethylene group,
$R_3$ and $R_4$ are ethyl groups, and
$R_5$ and $R_6$ are hydrogen atoms,
said compound being 1-(β-diethyl amino ethyl)-2-ethoxy carbonyl-3-ethoxy indole.

8. The indole compound of claim 1, in which
$R_1$ is the methoxy group,
$R_2$ is the methoxy carbonyl group,
A is the propylene group or the butylene group,
$R_3$ is the hydrogen atom, the methyl group, the ethyl group, or the isopropyl group,
$R_4$ is the hydrogen atom, the methyl group, the ethyl group, or the isopropyl group, and
$R_5$ and $R_6$ are hydrogen atoms,
said compound being a 2-methoxy carbonyl-3-methoxy indole compound which is substituted in 1-position by the β-dimethyl amino propyl group, the γ-amino propyl group, the γ-methyl amino propyl group, the γ-dimethyl amino propyl group, the γ-diethyl amino propyl group, the γ-isopropyl amino propyl group, the γ-di-isopropyl amino propyl group, or the γ-dimethyl amino butyl group.

9. The indole compound of claim 1, in which
$R_1$ is the methoxy group,
$R_2$ is the methoxy carbonyl group,
A is the propylene group,
$R_5$ and $R_6$ are hydrogen atoms, and
$R_3$ and $R_4$ are an alkylene group forming with the nitrogen atom to which they are attached, a pyrrolidine ring or a piperidine ring,
said compound being 2-methoxy carbonyl-3-methoxy indole compounds which are substituted in 1-position by the pyrrolidino propyl group or the piperidino propyl group.

10. The indole compound of claim 1, in which
$R_1$ is the methoxy group,
$R_2$ is the hydroxy carbonyl group,
A is the ethylene group,
$R_3$ and $R_4$ are methyl groups, and
$R_5$ and $R_6$ are hydrogen atoms,
said compound being 1-(β-dimethyl amino ethyl)-2-hydroxy carbonyl-3-methoxy indole.

11. The indole compound of claim 1, in which
$R_1$ is the methoxy group,
A is the ethylene group,
$R_3$ and $R_4$ are methyl groups,
$R_2$ is the amino carbonyl group, the methyl amino carbonyl group, the diethyl amino carbonyl group, or the di-isopropyl amino carbonyl group,
$R_5$ is the hydrogen atom, and
$R_6$ is the hydrogen atom or the methyl group,
said compound being a 1-(β-dimethyl amino ethyl)-3-methoxy indole compound which is substituted in 2-position by the amino carbonyl group, the methylamino carbonyl group, the di-ethyl amino carbonyl group, or the di-isopropyl amino carbonyl group, and which, in 5-position, is either unsubstituted or substituted by the methyl group.

12. The indole compound of claim 1, in which
$R_1$ is the hydroxyl group,
$R_2$ is the methoxy carbonyl group,
A is the ethylene group,
$R_3$ and $R_4$ are methyl groups,
$R_5$ is the hydrogen atom, and
$R_6$ is the hydrogen atom or the chlorine atom,
said compound being 1-(β-dimethyl amino ethyl)-2-methoxy carbonyl-3-hydroxy indole which, in 5-position, is either unsubstituted or substituted by the chlorine atom.

13. The indole compound of claim 1, in which
$R_1$ is the hydroxyl group,
$R_2$ is the ethoxy carbonyl group,
A is the propylene group,
$R_3$ and $R_4$ are ethyl groups, and
$R_5$ and $R_6$ are hydrogen atoms,
said compound being 1-(γ-diethyl amino propyl)-2-ethoxy carbonyl-3-hydroxy indole.

14. A pharmaceutical composition for treating motility disorders of the gastrointestinal tract comprising an effective amount of an N-amino alkyl indole compound of claim 1 and a pharmaceutically acceptable excipient.

15. In a method of treating motility disorders of the gastro-intestinal tract comprising administering an effective amount of an N-amino alkyl indole compound of claim 1.

* * * * *